US011071848B2

(12) United States Patent
Kirn et al.

(10) Patent No.: US 11,071,848 B2
(45) Date of Patent: Jul. 27, 2021

(54) NASAL BRIDLE CLIP APPLIER AND RELATED METHOD

(71) Applicant: Kirn Medical Design, LLC, Lexington, KY (US)

(72) Inventors: David S. Kirn, Lexington, KY (US); Kevin J Maudsley, Lexington, KY (US)

(73) Assignee: KIRN MEDICAL DESIGN, LLC, Lexington, KY (US)

(*) Notice: Subject to any disclaimer, the term of this patent is extended or adjusted under 35 U.S.C. 154(b) by 957 days.

(21) Appl. No.: 15/527,742

(22) PCT Filed: Nov. 24, 2015

(86) PCT No.: PCT/US2015/062468
§ 371 (c)(1),
(2) Date: May 18, 2017

(87) PCT Pub. No.: WO2016/086009
PCT Pub. Date: Jun. 2, 2016

(65) Prior Publication Data
US 2018/0015259 A1 Jan. 18, 2018

Related U.S. Application Data

(60) Provisional application No. 62/083,446, filed on Nov. 24, 2014.

(51) Int. Cl.
A61M 16/06 (2006.01)
A61M 25/02 (2006.01)

(52) U.S. Cl.
CPC ........ *A61M 25/02* (2013.01); *A61M 16/0666* (2013.01); *A61M 2025/024* (2013.01);
(Continued)

(58) Field of Classification Search
CPC ............ A61M 15/085; A61M 16/0666; A61M 16/0677; A61M 16/0683; A61M 16/0461;
(Continued)

(56) References Cited

U.S. PATENT DOCUMENTS 3,993,081 A * 11/1976 Cussell ............. A61M 16/0488
128/207.14
5,226,898 A 7/1993 Gross
(Continued)

Primary Examiner — Bradley H Philips
(74) Attorney, Agent, or Firm — Michael S. Hargis; King & Schickli, PLLC

(57) ABSTRACT

A receiver for securing at least one tube in a patient includes a shell operable in a first position for receiving the tube and a second position for securing the tube, and a compressible member supported by the shell for contacting the tube in the second position. A bridle looped around the patient's septum may also be secured in the second position. A system for securing the tube includes a receiver and an applier. The applier supports the receiver in the first position and transitions the receiver from the first position to the second position after the tube is positioned within the receiver. A method of securing a tube includes positioning the tube in a patient, placing a flexible member around the patient's nasal septum, receiving the tube and flexible member in a shell supported by an applier, and operating the applier to move the shell to a closed position.

10 Claims, 13 Drawing Sheets

(52) U.S. Cl.
CPC . *A61M 2025/0226* (2013.01); *A61M 2209/04* (2013.01); *A61M 2209/088* (2013.01)

(58) Field of Classification Search
CPC .......... A61M 16/0488; A61M 16/0497; A61M 16/0463; A61M 25/024; A61M 25/0226; A61M 2210/0618
See application file for complete search history.

(56) References Cited

U.S. PATENT DOCUMENTS

| | | | |
|---|---|---|---|
| 5,258,007 A | 11/1993 | Spetzler et al. | |
| 5,755,225 A * | 5/1998 | Hutson | A61M 25/02 128/207.18 |
| 6,099,536 A | 8/2000 | Petillo | |
| 6,336,457 B1 | 1/2002 | Hudson et al. | |
| 6,464,668 B1 * | 10/2002 | Pace | A61M 25/02 604/179 |
| 6,631,715 B2 * | 10/2003 | Kirn | A61M 16/0488 128/200.24 |
| 6,669,150 B2 | 12/2003 | Benoit et al. | |
| 6,837,237 B2 * | 1/2005 | Kirn | A61M 16/0488 128/200.24 |
| 8,056,868 B2 | 11/2011 | Vander Griend | |
| 8,512,312 B2 | 8/2013 | Sage | |
| 8,945,142 B2 | 2/2015 | Schaeffer et al. | |
| 2002/0026936 A1 | 3/2002 | Kirn | |
| 2005/0236001 A1 * | 10/2005 | Williams | A61M 25/02 128/207.18 |
| 2012/0271239 A1 * | 10/2012 | Andino | A61M 25/02 604/180 |
| 2013/0253540 A1 * | 9/2013 | Castro | A61B 17/1285 606/143 |
| 2013/0340764 A1 * | 12/2013 | Atkinson | A61M 25/02 128/207.18 |
| 2014/0005692 A1 | 1/2014 | Ellingwood et al. | |
| 2014/0261441 A1 * | 9/2014 | Phillips | A61M 16/0488 128/207.14 |
| 2017/0105904 A1 * | 4/2017 | Tatarek | A61J 15/0003 |

\* cited by examiner

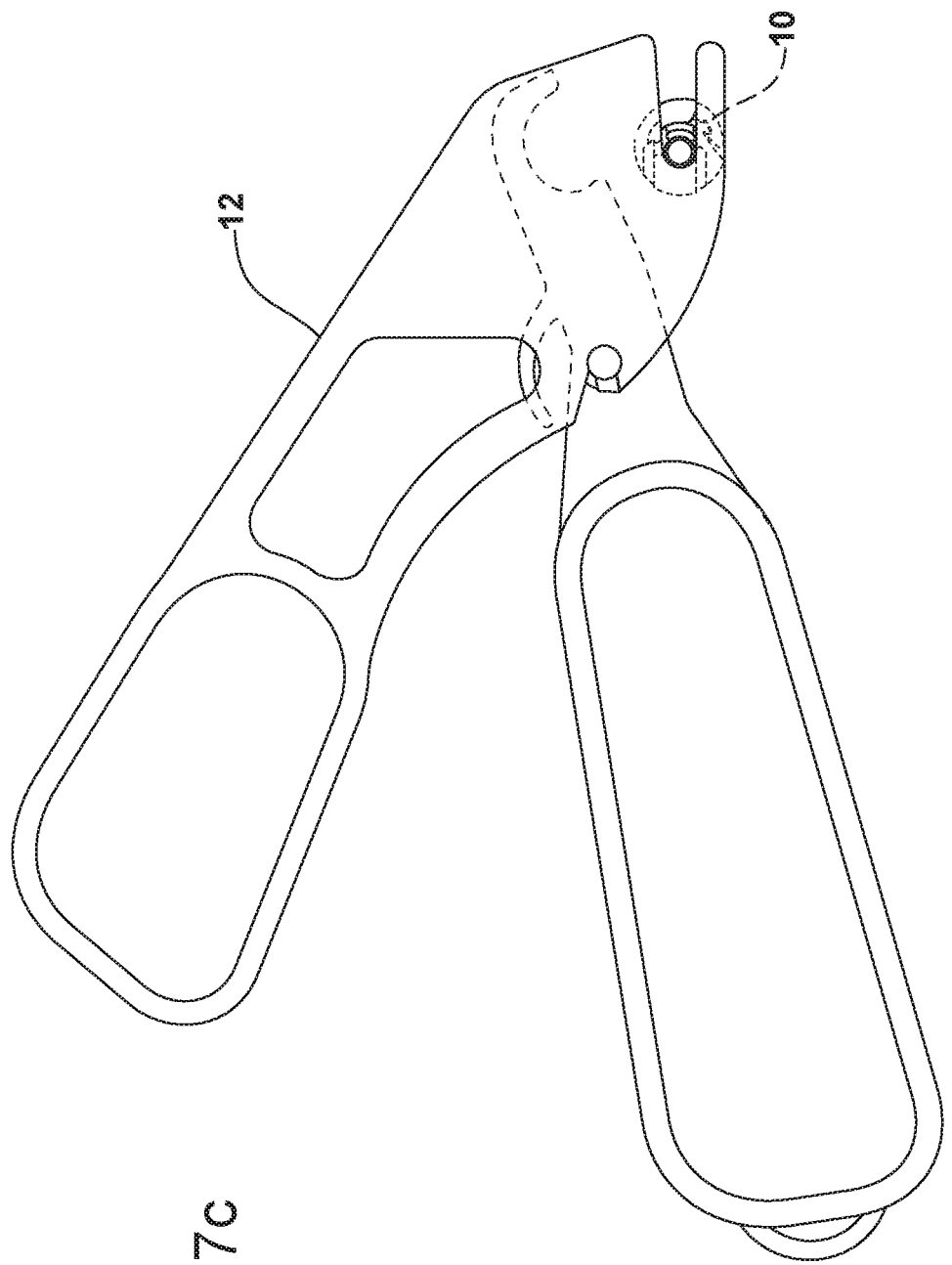

NASAL BRIDLE CLIP APPLIER AND RELATED METHOD

This application is the national stage of international patent application no. PCT/US2015/62468 filed on Nov. 24, 2015, which in turn claims priority from U.S. Provisional Patent Application Ser. No. 62/083,446 filed on Nov. 24, 2014, the disclosures of each of which are incorporated herein by reference in their entirety.

TECHNICAL FIELD

This document relates generally to a system for securing a tube positioned in a patient, and more specifically to a receiver and an applier for use in such a system.

BACKGROUND

A magnetic nasal tube bridle system has been previously described in U.S. Pat. Nos. 6,631,715 & 6,837,237. This system involves creating a loop of flexible material around the nasal septum. While the systems described in these patents are illustrative, a loop of flexible material can be positioned around a patient's nasal septum in any number of ways. The two ends of the loop are then anchored to a medical tube, whether a nasal tube or otherwise, to be retained by a clip. Existing clips are a bi-fold plastic design which clamps one or two ends of the flexible member extending around the septum and the tube together, often in a central channel. Such clips must be sized to fit the tube being retained as it must tightly adhere to the tube without slipping. In order to accommodate the multiple sized medical tubes in use, however, multiple corresponding clip sizes are manufactured and the user must select the appropriate size clip to retain a desired tube. Accordingly, there is a need for a clip which can accommodate multiple tube sizes, including non-standard tube sizes such as are commonly utilized in pediatric and neonatal applications.

Further, for neonatal and infant applications, there is need for a clip of overall smaller dimensions than existing models. In order to provide sufficient mechanical resistance against pulling of the tube, currently available clips can be difficult to close and potentially compress the lumen of the tube. Thus, an easier way to close and safely manipulate the small clip is needed.

The present invention seeks to provide a clip or receiver which accommodates multiple tube diameters and is sized appropriately for neonatal and newborn use. An applier may be included with this design to make positioning and closure of the clip easier. Retaining the clip within the applier until it is deployed, yields a safety benefit by minimizing the chance that the user will drop the clip into the patient (e.g., the patient's airway). Further, the clip may be re-opened, also using the application tool, re-loaded into the tool and re-applied to the tube as needed.

SUMMARY OF THE INVENTION

In accordance with the purposes and benefits described herein, a receiver for securing at least one tube in a patient is provided. The receiver includes a shell operable in a first position for receiving the at least one tube and a second position for securing the at least one tube, and a compressible member positioned supported by the shell for contacting the at least one tube in the second position.

In another possible embodiment, a first portion of the compressible member forms a recess for receiving the at least one tube in the first position.

In yet another possible embodiment, the first portion of the member contacts a first portion of the at least one tube through contact therewith and a second portion of the member contacts a second portion of the at least one tube in the second position.

In still another possible embodiment, the receiver further includes at least one band formed around the shell to secure the compressible member in position. In another, the at least one band includes a first band securing a distal end of the first portion of the compressible member and a second band securing a distal end of the second portion of the compressible member. In yet another, the at least one band includes first and second bands which are integrally formed with the compressible member.

In one other possible embodiment, the shell includes at least one boss.

In another possible embodiment, the shell includes a curved outer surface and first and second ends and the at least one boss includes at least a first boss extending from the first end and at least a second boss extending from the second end.

In one other possible embodiment, a system for securing at least one tube positioned in a patient includes a shell having at least one boss protruding therefrom, and an applier having at least one recess corresponding to the at least one boss for orienting the shell within the applier.

In yet another possible embodiment, the system further includes a compressible member supported by the shell for contacting the at least one tube in an engaged position.

In still another possible embodiment, the system further includes at least one band formed around the shell to secure the compressible member in position.

In another possible embodiment, the applier comprises first and second jaws. In still another, the first jaw is a moving jaw. In another, finger loops extend from the first and second jaws.

In one additional possible embodiment, the system further includes a closing member extending from the first jaw for contacting the shell and moving the shell from an open position to a closed position.

In one possible embodiment, a method of securing at least one tube positioned in a patient includes the steps of positioning a tube in a patient, placing a flexible member around the patient's nasal septum, receiving the at least one tube and at least one end of the flexible member in a shell supported by an applier, and operating the applier to move the shell from a first position for receiving the at least one tube and at least one end of the flexible member to a second position for securing the at least one tube and at least one end of the flexible member.

In another possible embodiment, the applier includes first and second jaws, and the step of operating the applier includes moving one of the first and second jaws causing contact with the receiver sufficient to move the receiver from the first position to the second position.

In still another possible embodiment, the method further includes the step of ejecting the receiver from the applier.

In yet another possible embodiment, the applier includes first and second jaws, and the step of operating the applier includes moving one of the first and second jaws from an initial position to an intermediary position such that contact between the one of the first and second jaws and the receiver during movement between the initial position and the intermediary position causes the receiver to move from the first position to the second position, and subsequently moving the one of the first and second jaws from the intermediary position to a final position such that contact between the first and second jaws during movement between the intermediary position and the final position causes the receiver to be ejected from the applier.

In one other possible embodiment, the receiver includes at least one boss and the applier includes at least one recess for receiving the boss.

In the following description, there are shown and described several possible embodiments of the receiver, system and related method of securing a tube positioned in a patient. As it should be realized, the receivers, systems and methods are capable of other, different embodiments and their several details are capable of modification in various, obvious aspects all without departing from the invention as set forth and described in the following claims. Accordingly, the drawings and descriptions should be regarded as illustrative in nature and not as restrictive.

BRIEF DESCRIPTION OF THE DRAWING FIGURES

The accompanying drawing figures incorporated herein and forming a part of the specification, illustrate several aspects of the receiver, system and related method of securing a tube positioned in a patient, and together with the description serve to explain certain principles thereof. In the drawing figures:

FIG. 7C is a side elevational view showing the applier in a third position to allow the receiver to be ejected after closure;

Reference will now be made in detail to the present described embodiments of the receivers, systems and related methods of securing a tube positioned in a patient, examples of which are illustrated in the accompanying drawing figures, wherein like numerals are used to represent like elements.

DETAILED DESCRIPTION

Broadly speaking, the described invention includes a receiver or clip 10 for securing at least one tube positioned in a patient. The at least one tube may be a temporary tube placed into the gastrointestinal or respiratory tracts of the patient or otherwise. Such tubes typically enter the patient via the nose or mouth. A system for placing securing at least one tube in a patient includes the receiver 10 and an application tool or applier 12. Each of the receiver 10 and the applier 12 have multiple component parts and features as described below.

Figure 1A:
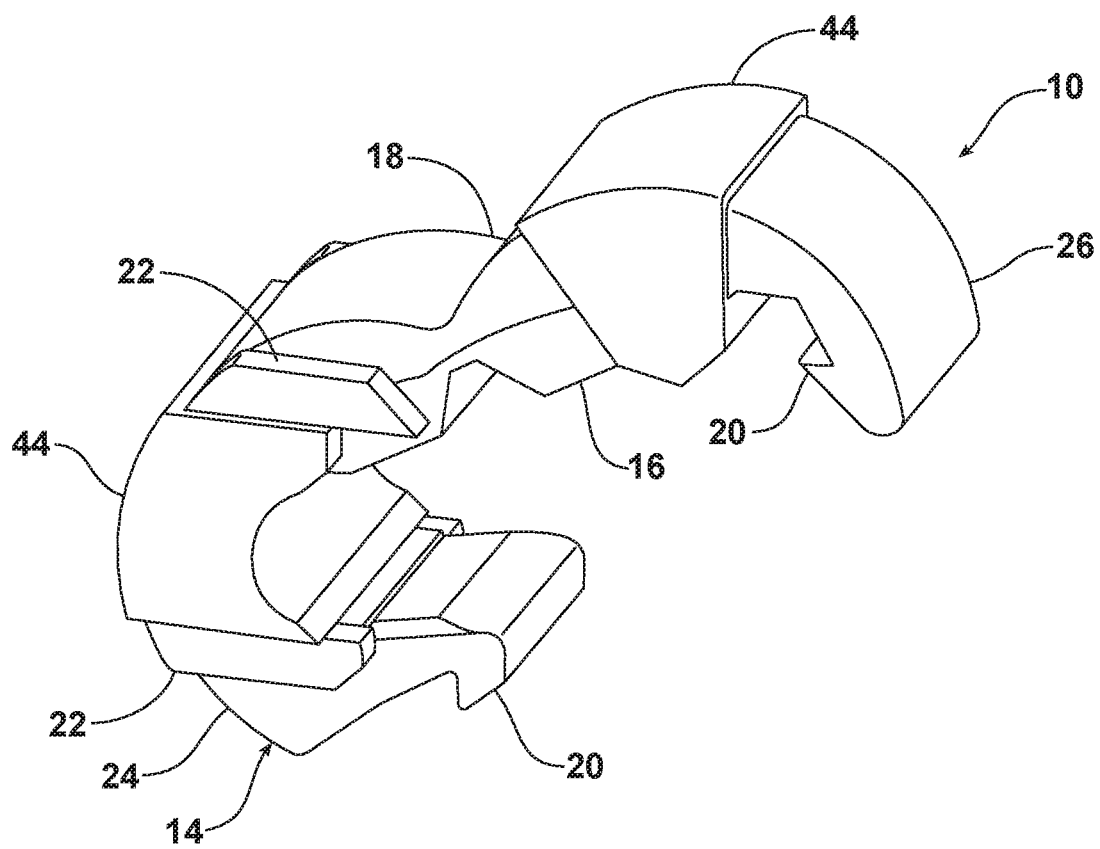
FIGS. 1A and 1B are an illustrated perspective views of a receiver in a first open position.
Figure 1B:
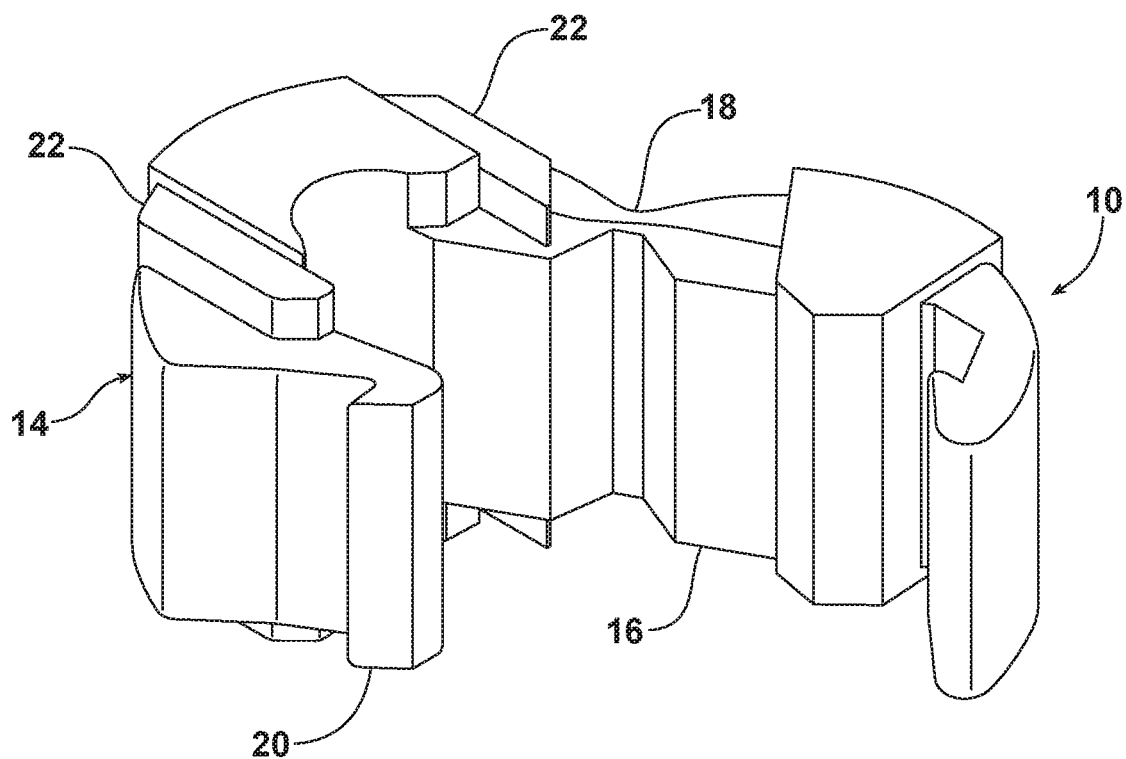

As shown in FIGS. 1A and 1B, the receiver 10 includes a shell 14 operable in a first position to receive at least one tube and a second position to secure the at least one tube, and a member or insert 16 supported by or positioned within the shell and contacting the at least one tube in the second position. The shell 14 further includes a hinge 18, a locking mechanism 20, and bosses 22 protruding from the shell to orient or locate the shell in the application tool or applier 12. More specifically, a molded plastic shell 14 includes first and second pivotally connected parts 24, 26. In the described embodiment, the hinge 18 is a living hinge integrally formed with the first and second parts 24, 26 which allows the shell 14 to move from the first to the second position.

Figure 2:
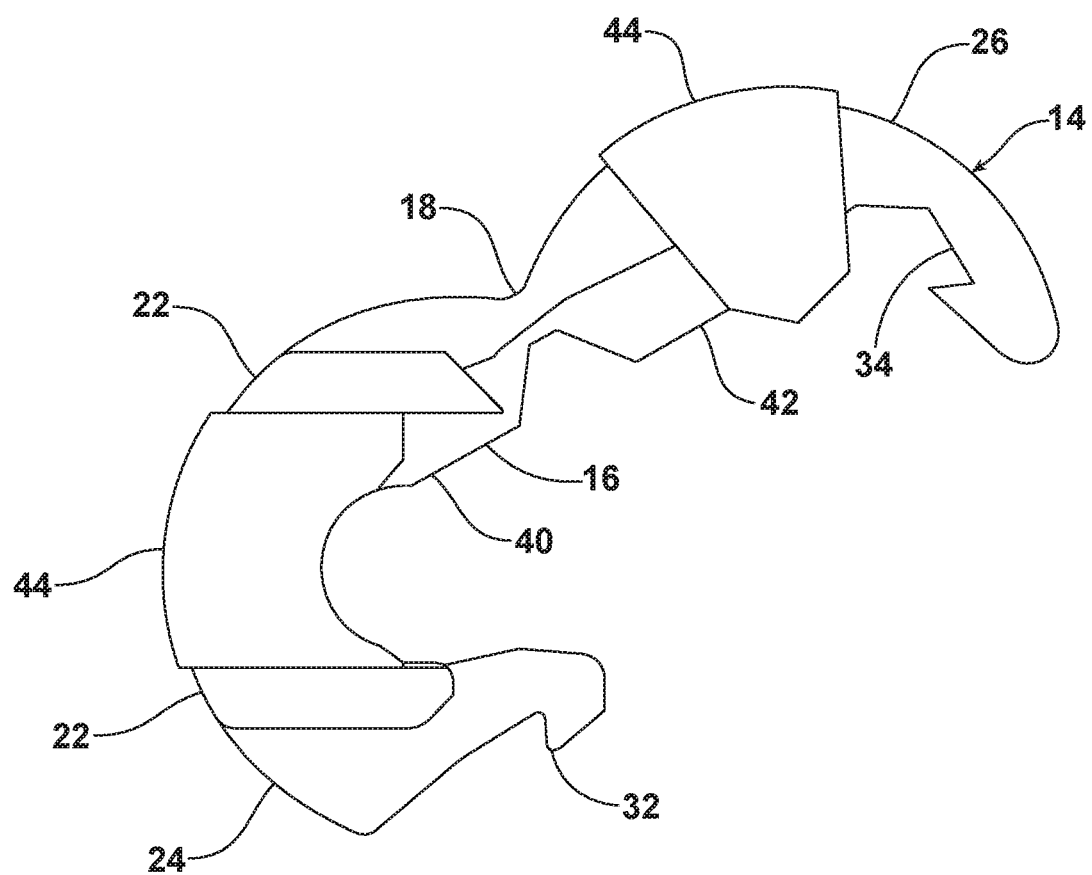
FIG. 2 is a side elevational view of the receiver in the first open position.

The shell 14 is generally U-shaped in the first, or open, position, in the described embodiment, as best shown in FIG. 2. In this position, the shell 14 is open for receiving a tube 28 and at least one end of bridle flexible members. In the second, or closed, position shown in FIG. 3, the first and second parts 24, 26 are further connected by the locking mechanism 20 and the tube 28 and the bridle flexible members 30 may reside centrally within the receiver 10 when in the second or closed position.

Figure 3:
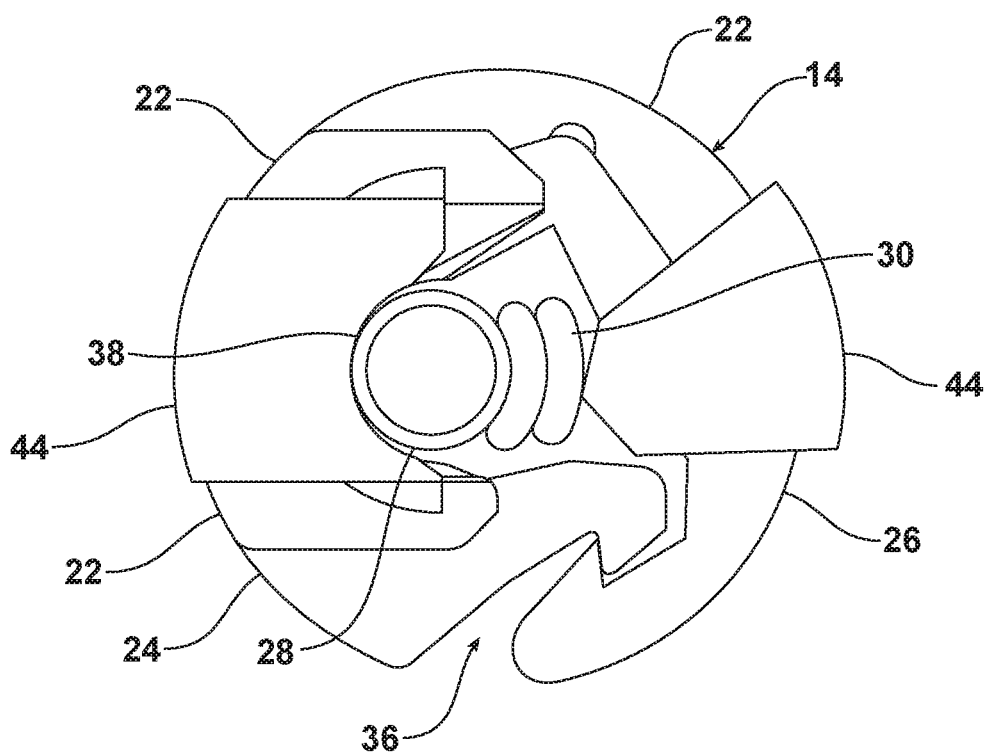
FIG. 3 is a side elevational view showing the receiver in a second closed position.

The described locking mechanism 20, shown in FIGS. 2 and 3, is a snap joint including a hook 32 positioned along a distal end of the first part 24 of the shell 14 and a depression 34 formed in a distal end of the second part 26 of the shell for receiving the hook in the closed position. In this position, the shell 14 is substantially cylindrical or circular in shape and the first and second parts 24, 26 of the shell 14 form a substantially wedge shaped aperture 36 used to unlock the receiver to remove the tube and bridle flexible member(s).

The described insert 16 is made of a compressible material. In this embodiment, the compressible material is a silicone rubber in order to be inert to the human body. The geometry of the insert 16 can vary so long as the insert may be maintained in position within the shell 14. A recess 38 in the insert 16 may be sized to fit a single tube size or a range of sizes. For example, one insert 16 will accommodate size 8 French tubes while another may accommodate 5 and 6 French tubes. Due to the compressible nature of the silicone rubber, the insert 16 may also accommodate tubes of non-standard size. An 8 French insert 16, for example, should fit a tube having an OD just larger or just smaller than that of an 8 Fr. tube. In the described embodiment, the recess 38 is designed to accommodate a range of tube sizes. For instance, one insert 16 having recess 38 may accommodate a 5, 6, or 8 French tubes. This may be accomplished by increasing an amount of silicone behind the recess 38.

Referring back to FIG. 2, the insert 16 includes first and second portions 40, 42 which substantially conform to mating surfaces on inner surfaces of the first and second parts 24, 26 of shell 14. Adhesives may, as well as friction due to compression, serve to keep the insert 16 in place. In the described embodiment, however, the first and second portions 40, 42 include bands 44 formed around the shell 14 during a second molding step to secure the insert 16 in position. In an alternate embodiment, the first and second parts 24, 26 of shell 14 and insert 16 may be integrally molded utilizing an insert molding technique.

The compressible nature of the silicone rubber used for the insert 16 allows insertion of the tube 28 and the end(s) of the flexible member 30 in any order or position within the space available for them. Further, the silicone rubber grips the tube 28 and flexible member end(s) 30 with greater friction than a harder plastic thereby providing greater resistance against the tube and/or the flexible member ends slipping out. This allows the overall size of the receiver 10 to be minimized while providing sufficient retentive force without compressing the lumen of tube 28.

Figure 4:
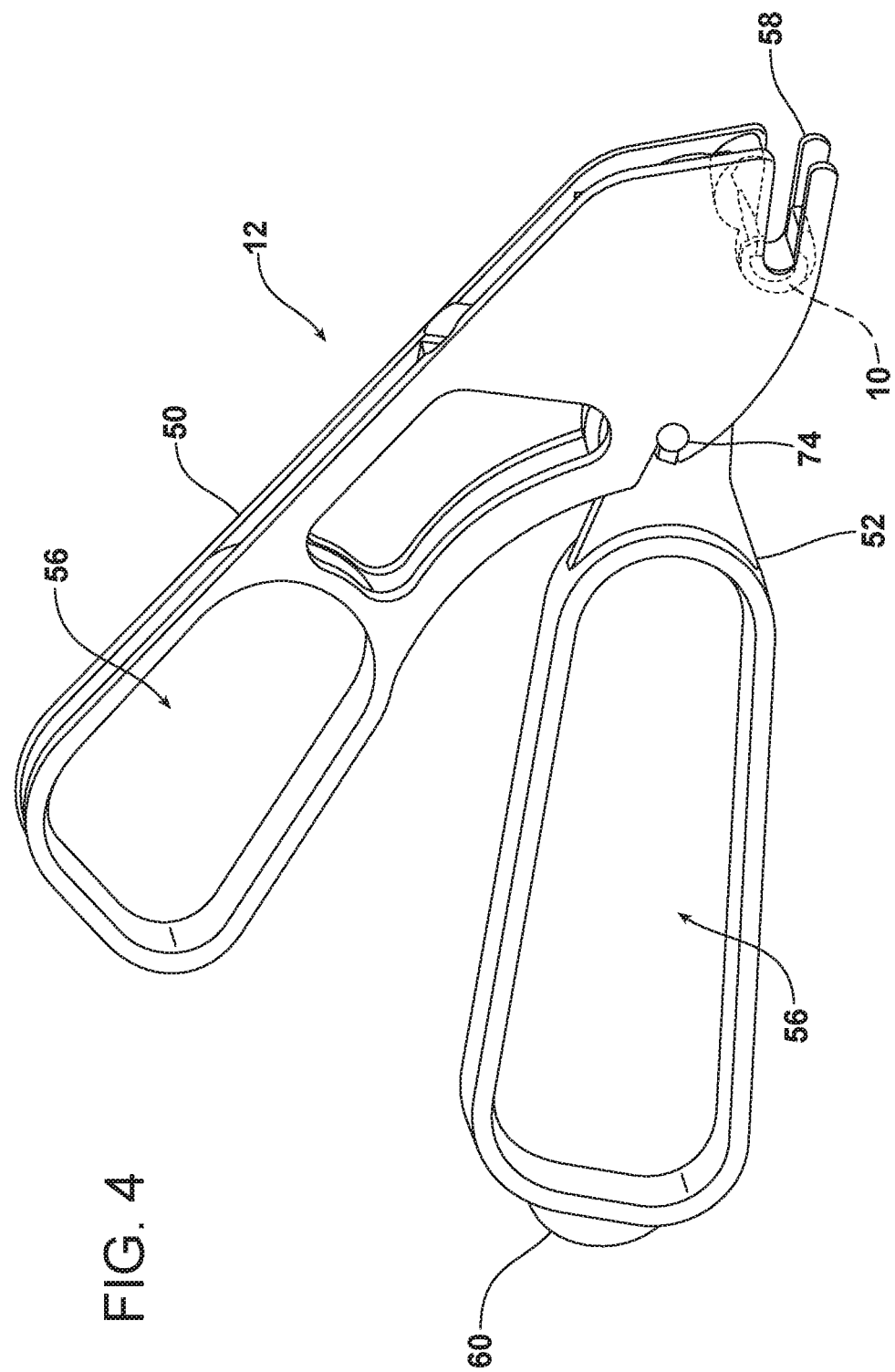
FIG. 4 is an illustrated perspective view of an applier supporting the receiver in the first open position.

The application tool 12 is shown partially transparent in FIG. 4 with the receiver 10 retained. This is an "as supplied" configuration in the described embodiment. The described application tool 12 consists of two components including a static jaw 50 and moving jaw 52. The static jaw 50 holds the receiver 10 in the first open position and the moving jaw 52 moves the second shell part 26 to the second closed position when the user moves the finger loops 56 closer together. Guides 58 are provided to guide or facilitate insertion of the tube 28 and the flexible member end(s) 30 into the proper location for closure of the receiver 10. The application tool 12 also includes a wedge 60 for opening the receiver 10. The wedge 60 fits into the substantially wedge shaped aperture 36 to unlock or disengage the locking mechanism 20 and open the receiver 10.

Figure 5:
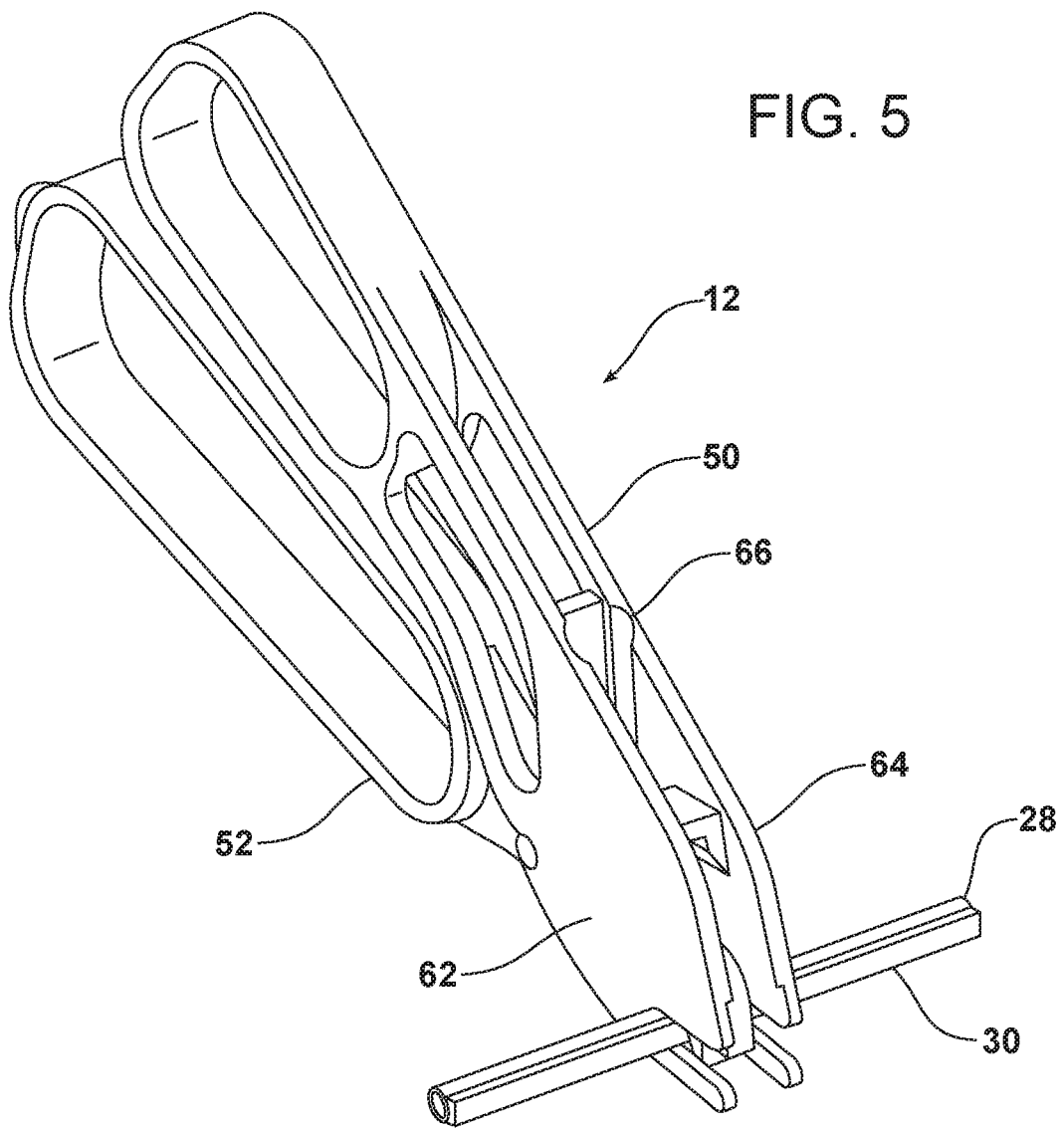
FIG. 5 is an illustrated perspective view of the applier supporting the receiver and a medical tube in the second closed position.
Figure 6:
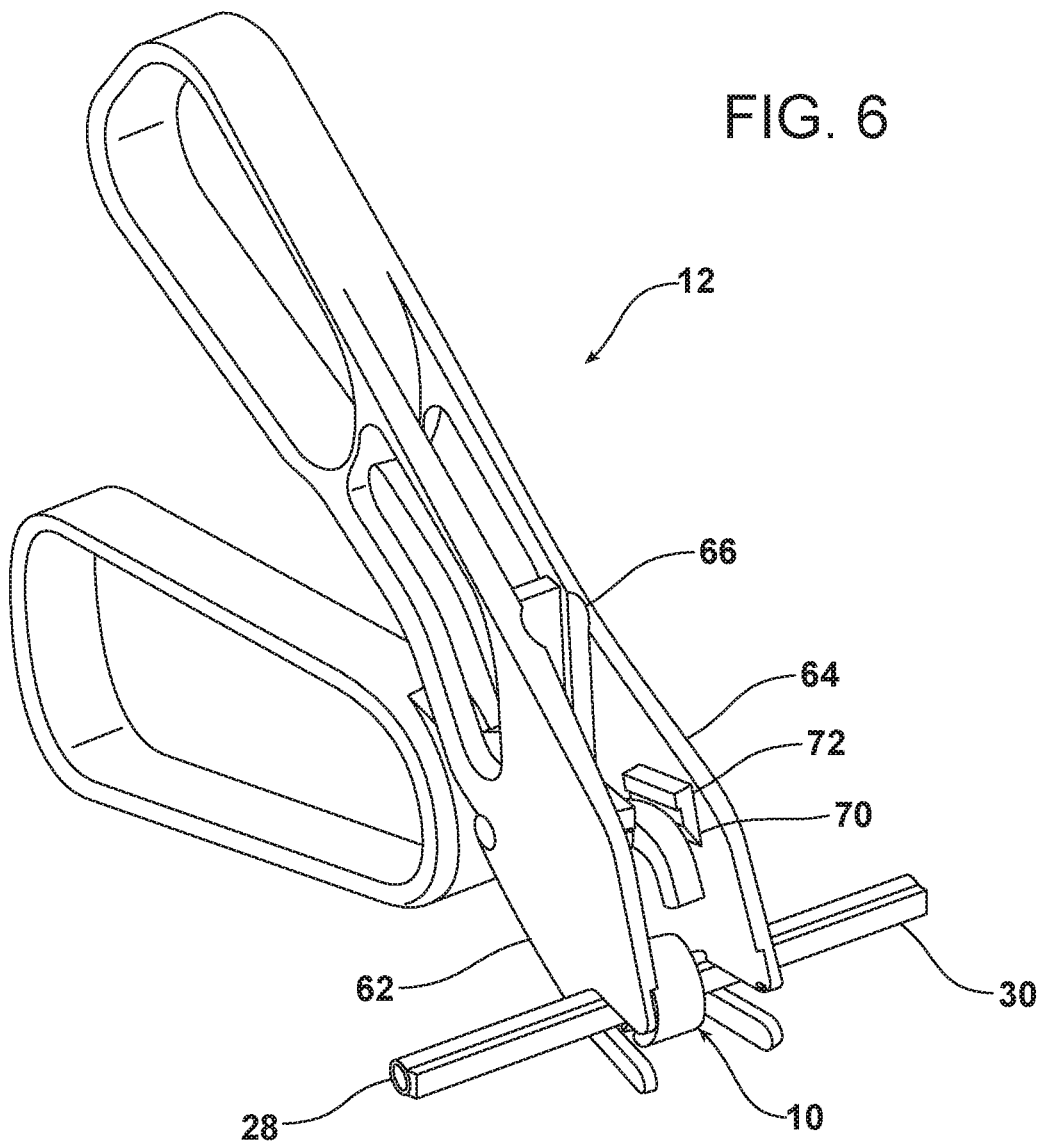
FIG. 6 is an illustrated perspective view of the applier supporting the receiver after closure of the receiver showing the flexing of the applier to allow the receiver to be ejected after closure.

As shown in FIGS. 5 and 6, the static jaw 50 is divided into a left half 62 and a right half 64 on one end to provide a retention clamp for receiver 10. Living hinges 66 allow the left half 62 and right half 64 to spread apart allowing for insertion or removal of the receiver 10. The bosses 22 on the sides of the shell 14 fit into corresponding recesses 68 (best shown in FIG. 10) on an interior aspect of the left half 62 and the right half 64. Ramps 70, shown in FIG. 6, spread the left half 62 and the right half 64 apart so that the receiver 10 may be ejected from the application tool 12. A distal portion of the moving jaw 52 impinges upon the ramps 70 to spread the left and right halves 62, 64 apart. Eject stop 72 provides a limit to maximum opening.

Figure 7A:
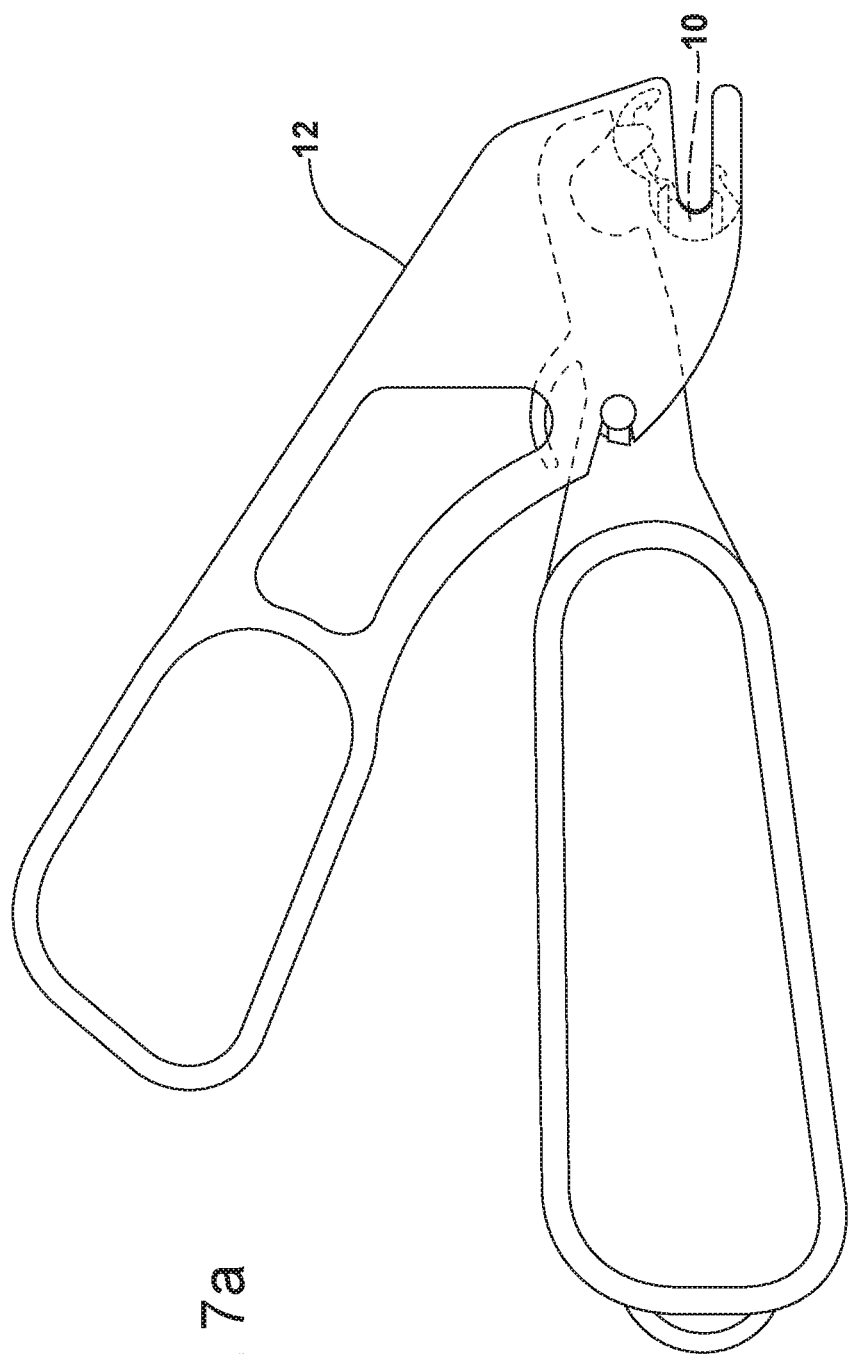
FIG. 7A is a side elevational view showing the applier in a first position with the receiver in the first open position.
Figure 7B:
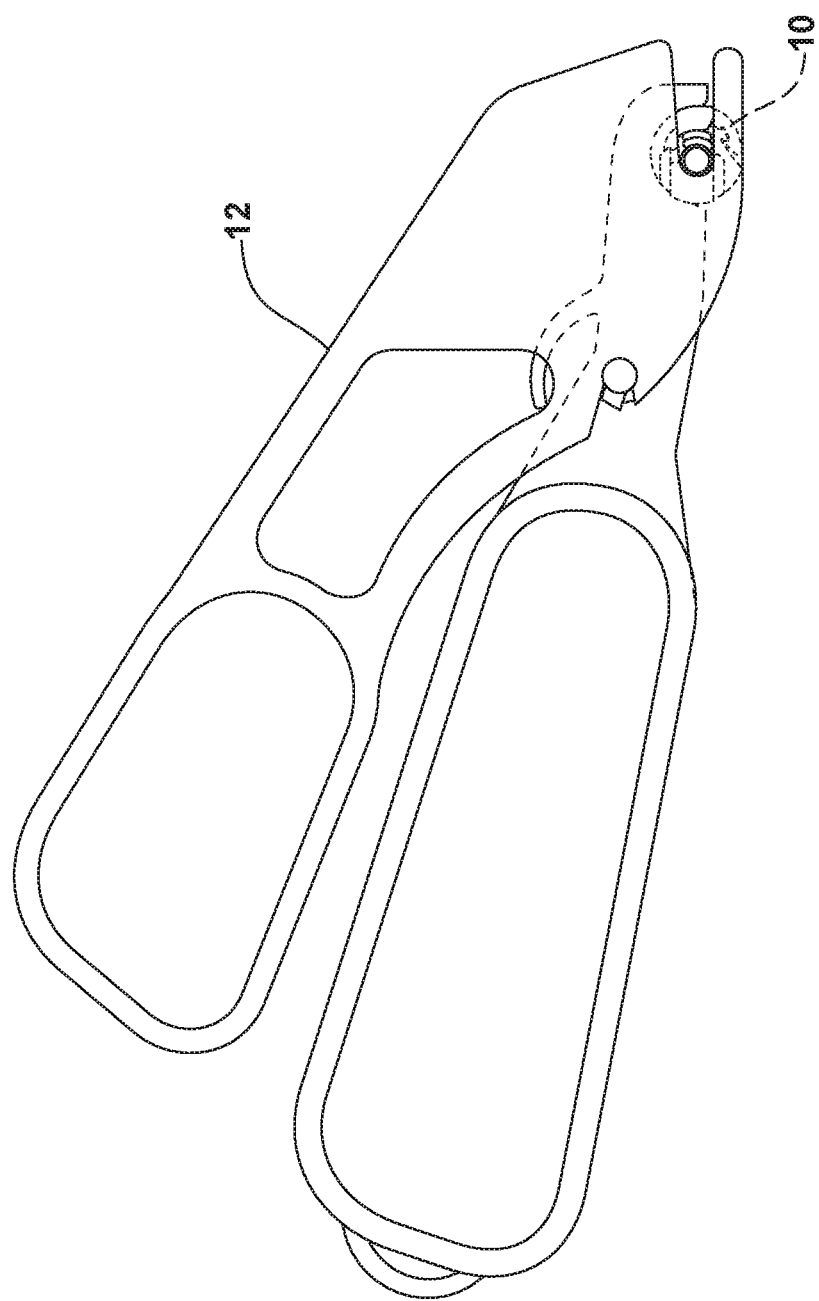
FIG. 7B is a side elevational view showing the applier in a second position with the receiver in the second closed position.

FIG. 7 illustrates three positions of the system with the static jaw 50 shown semi-transparent for illustrative purposes. More specifically, FIG. 7A shows the receiver 10 and applier 12 in an "as supplied" position. FIG. 7B shows the applier 12 after closing the receiver 10 around a tube and FIG. 7C shows the applier 12 in an ejection position where the closed receiver may be ejected from the applier.

Figure 8:
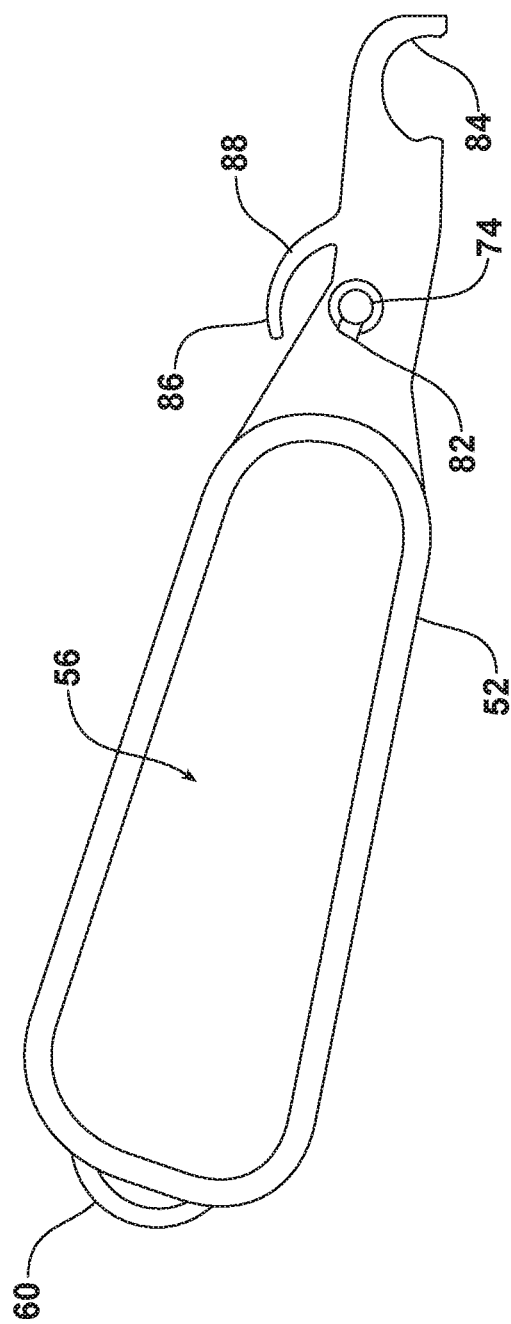
FIG. 8 is a side elevational view showing a first moving jaw of the applier.
Figure 9:
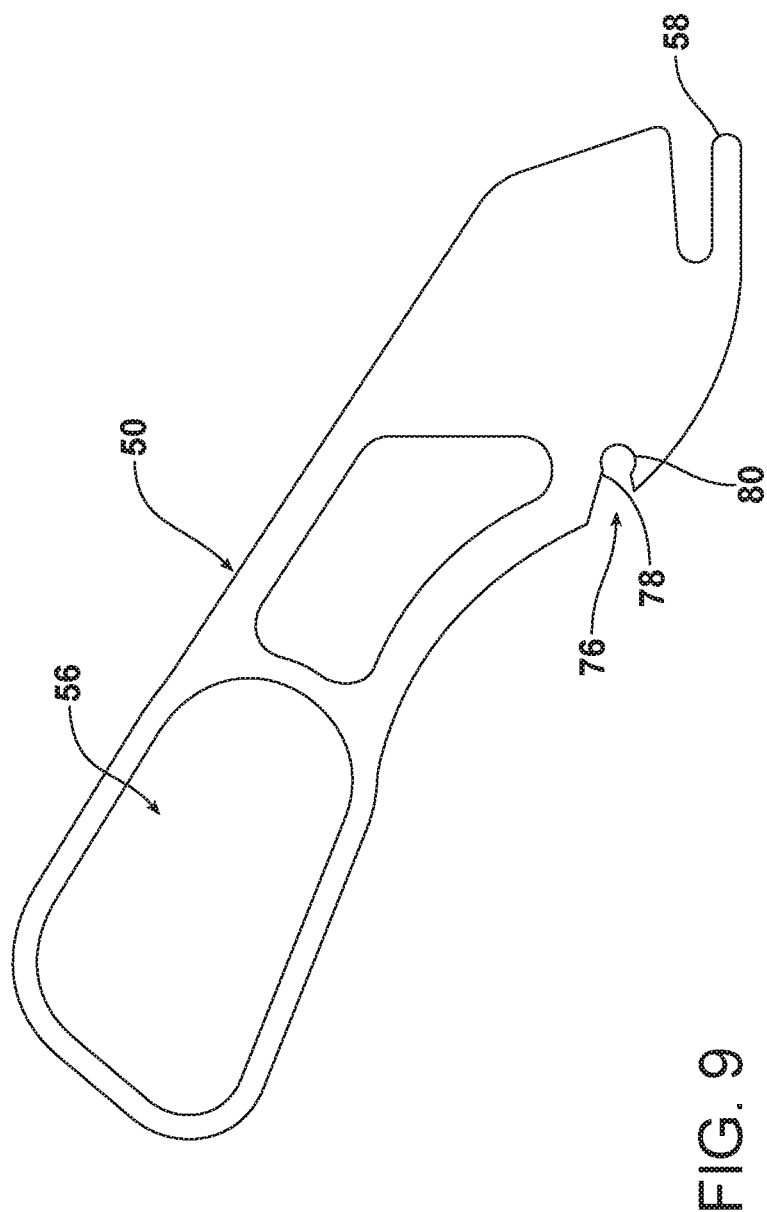
FIG. 9 is a side elevational view showing a second static jaw of the applier.

As shown in FIGS. 4, 8, and 9, the static jaw 50 and moving jaw 52 are connected via axle 74. The axle 74 fits into an open recess 76 on the static jaw 50 allowing for rotational motion between the two jaws. A neck 78 of the recess 76 is slightly narrower than the axle 74 thereby maintaining the axle within the recess 76 and concentric within the larger circular apex 80 of the recess. The axle 74 is integrally molded in the moving jaw 52. This arrangement provides easy assembly and minimizes the cost of manufacture rather than, for example, heat staking or need of a separate hinge pin part. Nonetheless, these alternate embodiments are encompassed in the broader invention. An axle stop 82 limits the rotational range of motion of the two jaws 50, 52 relative to one another to prevent excessive closing or opening/eject. The axle stop 82 impinges on the sides of the recess 76 to limit the motion.

As shown in FIG. 8, the moving jaw 52 includes a closing arc 84 which moves or pushes the shell 14 closed after insertion of the tube 28 and the flexible member end(s) 30. An integrally molded indexing detent 88 is located on arcuate projection 86. The detent 88 prevents unwanted motion of the two jaws 50, 52 in the "as supplied" position and gives the user a definitive feedback which is palpable and audible when transitioning from open, to closed, to eject positions.

As shown in FIG. 9, the static jaw 50 includes guides 58 to guide or facilitate insertion of the tube 28 and the flexible member end(s) 30 into the proper location for closure of the receiver 10. The static jaw 50 further includes the recess 76 which receives the axle 74 and allows for rotational motion between the two jaws.

Figure 10:
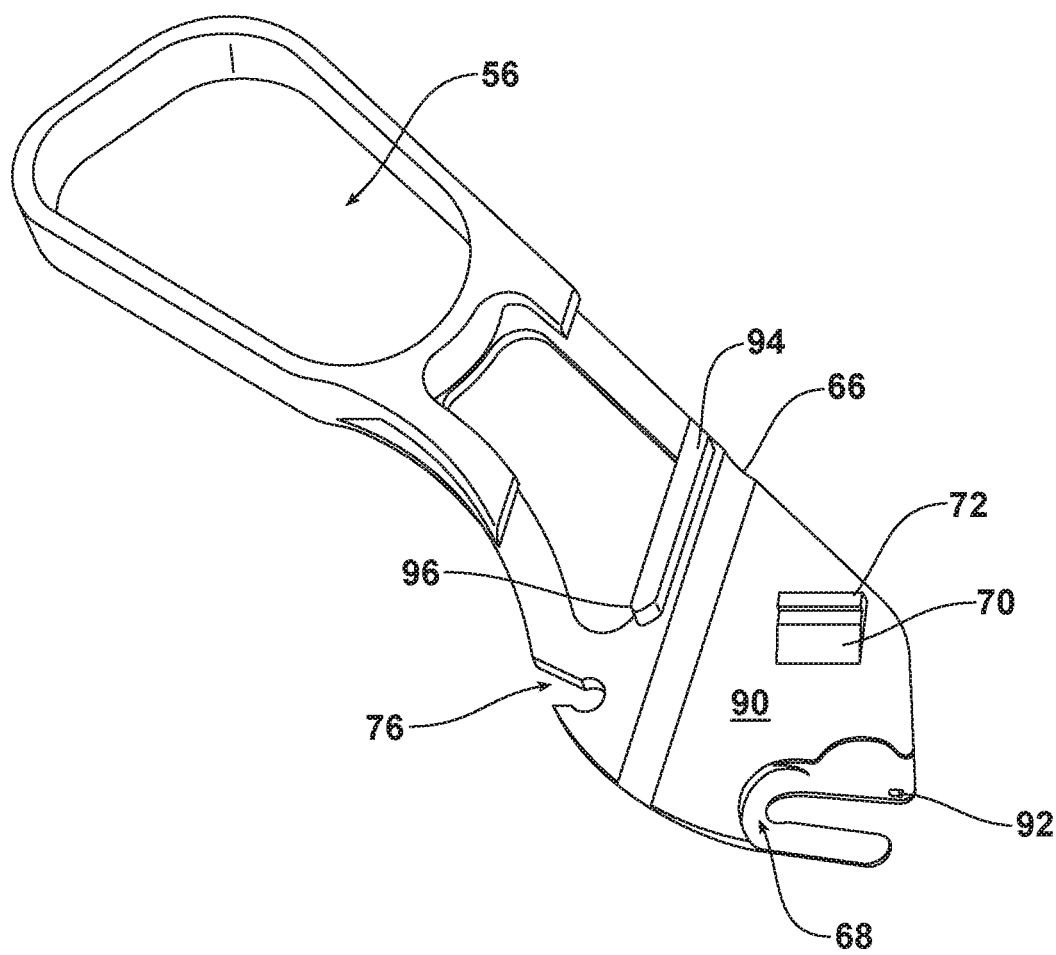
FIG. 10 is an illustrated perspective view of the second static jaw of the applier.

An interior surface 90 of the static jaw 50 is partially shown in FIG. 10. The recesses 68 receive the bosses 22 on the sides of the shell 14 and it is of note that the recesses are at two levels. Thus, the shell 14 is removably retained in this area in the open position until the moving jaw 52 is activated. A shell retention boss 92 prevents the moving portion of the shell 14 from falling down and partially closing. The left half 62 and the right half 64 are connected distal to the static jaw living hinge 66 by connection bar 94. A first portion 96 of the connection bar 94 serves as an index point against the arcuate projection 86. The eject ramp 70 and stop 72 are also shown.

As indicated above, the system is supplied to the user with the receiver 10 positioned in the open position in the applier 12. In addition to the mechanism utilizing the arcuate projection 86 and its index system, the system may also be shipped in a custom package to avoid premature closure. Prior to using the receiver 10 and the applier 12, a bridle loop and tube have already been inserted into the patient. The user then selects an appropriately sized receiver. The only difference from one size to the next is a configuration of the insert 16. Specifically, the diameter of the recess 38 and the thickness of the insert are sized to a specific tube size or a range of tube sizes.

The user then positions the application 12 tool such that the tube slides in between the guides 58. Likewise, bridle flexible members are positioned using the guides 58. When all three components are in position within the shell 14, the user closes the receiver 10 by moving finger loops 56 of the two jaws 50, 52 together. An audible clicking sound is heard as well as a tactile signal felt indicating that the receiver 10 has reached the closed position.

Next, the user will move the finger loops 56 apart, first back to the open position and then further motion in the same direction forces the moving jaw 52 between ramps 70 thereby spreading apart the left half 62 and the right half 64 of the static jaw 50 to an ejection position. In this ejection position, the receiver 10 is now free to exit the application tool 12 and can move out of the recesses 68 which have been holding it in place. Thus, the tube and the bridle loop flexible members are locked in place in the receiver 10. For added security, the user may choose to tie a knot in the flexible members or may tie the flexible members together and secure only one end within the receiver 10. Of course, redundant length of the flexible member(s) may be trimmed.

Should the user wish to open the receiver 10, for example to reposition the tube 28, opening wedge 60 may be used. Opening wedge 60 is inserted into the substantially wedge shaped aperture 36 used to unlock the receiver which forces the locking mechanism 20 open and the receiver 10 to return to the first or open position. The receiver may then be replaced into application tool 12 for replacement if desired. The user could also place and close the receiver 10 manually, however this is not recommended.

The foregoing has been presented for purposes of illustration and description. It is not intended to be exhaustive or to limit the embodiments to the precise form disclosed. Obvious modifications and variations are possible in light of the above teachings. For example, the insert may generally take the shape of a tongue which extends outward from a main body. The tongue may be designed to wrap around the tube and at least one of the ends of the flexible member when the shell is in the closed position. The tongue may be held captive and guided by the shell to bend around the tube and flexible members by stabilizing rails during closing. All such modifications and variations are within the scope of the appended claims when interpreted in accordance with the breadth to which they are fairly, legally and equitably entitled.

What is claimed:

1. A system for securing at least one tube positioned in a patient, comprising:
   a shell having at least one boss protruding therefrom;
   an applier having at least one recess corresponding to said at least one boss for orienting said shell within said applier;
   a compressible member supported by said shell for contacting the at least one tube in an engaged position; and
   at least one band formed around said shell to secure said compressible member in position.

2. The system for securing the at least one tube positioned in a patient of claim 1, wherein said applier comprises first and second jaws.

3. The system for securing the at least one tube positioned in a patient of claim 2, wherein said first jaw is a moving jaw.

4. The system for securing the at least one tube positioned in a patient of claim 2, wherein finger loops extend from said first and second jaws.

5. The system for securing the at least one tube positioned in a patient of claim 2, further comprising a closing member extending from said first jaw for contacting said shell and moving said shell from an open position to a closed position.

6. A method of securing at least one tube positioned in a patient, comprising the steps of:
   positioning a tube in a patient;
   placing a flexible member around the patient's nasal septum;
   receiving the at least one tube and at least one end of said flexible member in a shell supported by an applier; and
   operating said applier to move said shell from a first position for receiving the at least one tube and at least one end of said flexible member to a second position for securing the at least one tube and at least one end of said flexible member.

7. The method of securing at least one tube positioned in a patient of claim 6, wherein said applier includes first and second jaws, and the step of operating said applier includes moving one of said first and second jaws causing contact with the shell sufficient to move the shell from the first position to the second position.

8. The method of securing at least one tube positioned in a patient of claim 7, further comprising the step of ejecting the shell from said applier.

9. The method of securing at least one tube positioned in a patient of claim 6, wherein said applier includes first and second jaws, and the step of operating said applier includes moving one of said first and second jaws from an initial position to an intermediary position such that contact between said one of said first and second jaws and the shell during movement between the initial position and the intermediary position causes the shell to move from the first position to the second position, and subsequently moving said one of said first and second jaws from the intermediary position to a final position such that contact between said first and second jaws during movement between the intermediary position and the final position causes the shell to be ejected from said applier.

10. The method of securing at least one tube positioned in a patient of claim 6, wherein the shell includes at least one boss and said applier includes at least one recess for receiving said boss.

* * * * *